United States Patent [19]

Ben-Bassat et al.

[11] Patent Number: 4,656,132
[45] Date of Patent: Apr. 7, 1987

[54] METHOD OF IMPROVING THE YIELD OF HETEROLOGOUS PROTEIN PRODUCED BY CULTIVATING RECOMBINANT BACTERIA

[75] Inventors: Arie Ben-Bassat, Concord; Glenn Dorin, San Rafael; Keith Bauer, Oakland; Leo Lin, Fremont, all of Calif.

[73] Assignee: Cetus Corporation, Emeryville, Calif.

[21] Appl. No.: 594,250

[22] Filed: Mar. 28, 1984

[51] Int. Cl.[4] ..................... C12P 21/00; C12N 15/00
[52] U.S. Cl. .................................. 435/68; 435/172.3; 935/33; 935/38; 935/111
[58] Field of Search ................. 424/85; 435/172.3, 68, 435/317, 240, 241, 70, 71, 244, 247, 811; 935/33, 38, 111

[56] References Cited

FOREIGN PATENT DOCUMENTS 0014050 8/1980 European Pat. Off. ............... 435/68
0036776 9/1981 European Pat. Off. ......... 435/172.3

OTHER PUBLICATIONS

Ingram, 1976, *J. Bact.* v 125 (2) 670–678.
Lee et al, 1983, Proc Natl Acad Sci, v 80, 7496–7500.

*Primary Examiner*—Thomas G. Wiseman
*Assistant Examiner*—Joanne M. Giesser
*Attorney, Agent, or Firm*—Albert P. Halluin

[57] ABSTRACT

A method for improving the yield of heterologous protein such as IFN-α, IFN-β, and IL-2, produced by recombinant bacteria by supplementing the nutrient medium in which the bacteria are grown with a water soluble alcohol and/or amino acid mixture during the terminal phase of the cultivation.

10 Claims, 2 Drawing Figures

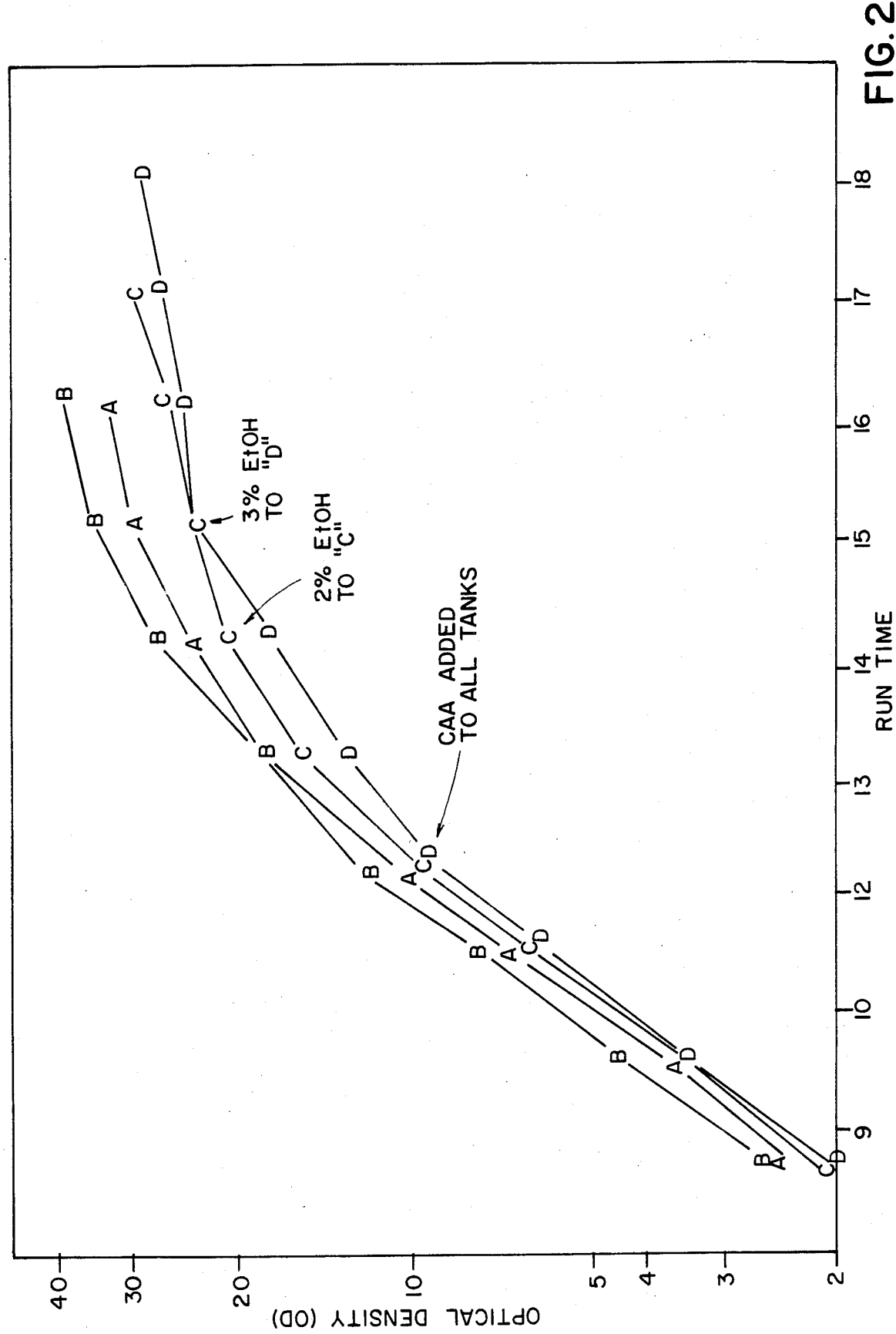

METHOD OF IMPROVING THE YIELD OF HETEROLOGOUS PROTEIN PRODUCED BY CULTIVATING RECOMBINANT BACTERIA

DESCRIPTION

1. Technical Field

This invention is in the field of biochemical engineering. More particularly it relates to a process for cultivating heterologous protein-producing recombinant cells such that the yield of the heterologous protein is improved.

2. Background Art

Synthetic and chemically defined media for cultivating microorganisms are well known. Conventional nutrient media for cultivating bacteria have been used to grow recombinant bacteria that are capable of producing heterologous polypeptides. See, for instance, European patent application No. 81301227.5 (published under number 0036776 on 30 September 1981) and copending commonly owned U.S. application Ser. No. 375,098 filed May 5, 1982. Casamino acids have been included in such nutrient media throughout the cultivation period.

Ethanol is known to have various effects on E. coli metabolism. See Ingram, L. O., *J Bacteriol* (1976) 125:670–678 and Lee, P. C., et al, *PNAS (USA)* 80:7496–7500.

DISCLOSURE OF THE INVENTION

The invention concerns a method of improving the yield of heterologous protein produced by cultivating recombinant bacteria in a liquid nutrient medium comprising supplementing the medium with an effective amount of a water soluble alkanol of 1 to 4 carbon atoms and/or a mixture of amino acids that supports bacterial growth during the terminal portion of the cultivation.

BRIEF DESCRIPTION OF THE DRAWINGS

In the drawings

FIG. 2 is a graph of OD$_{680}$ versus run time for the fermentations described in Example 3, infra.

MODES FOR CARRYING OUT THE INVENTION

Figure 1:
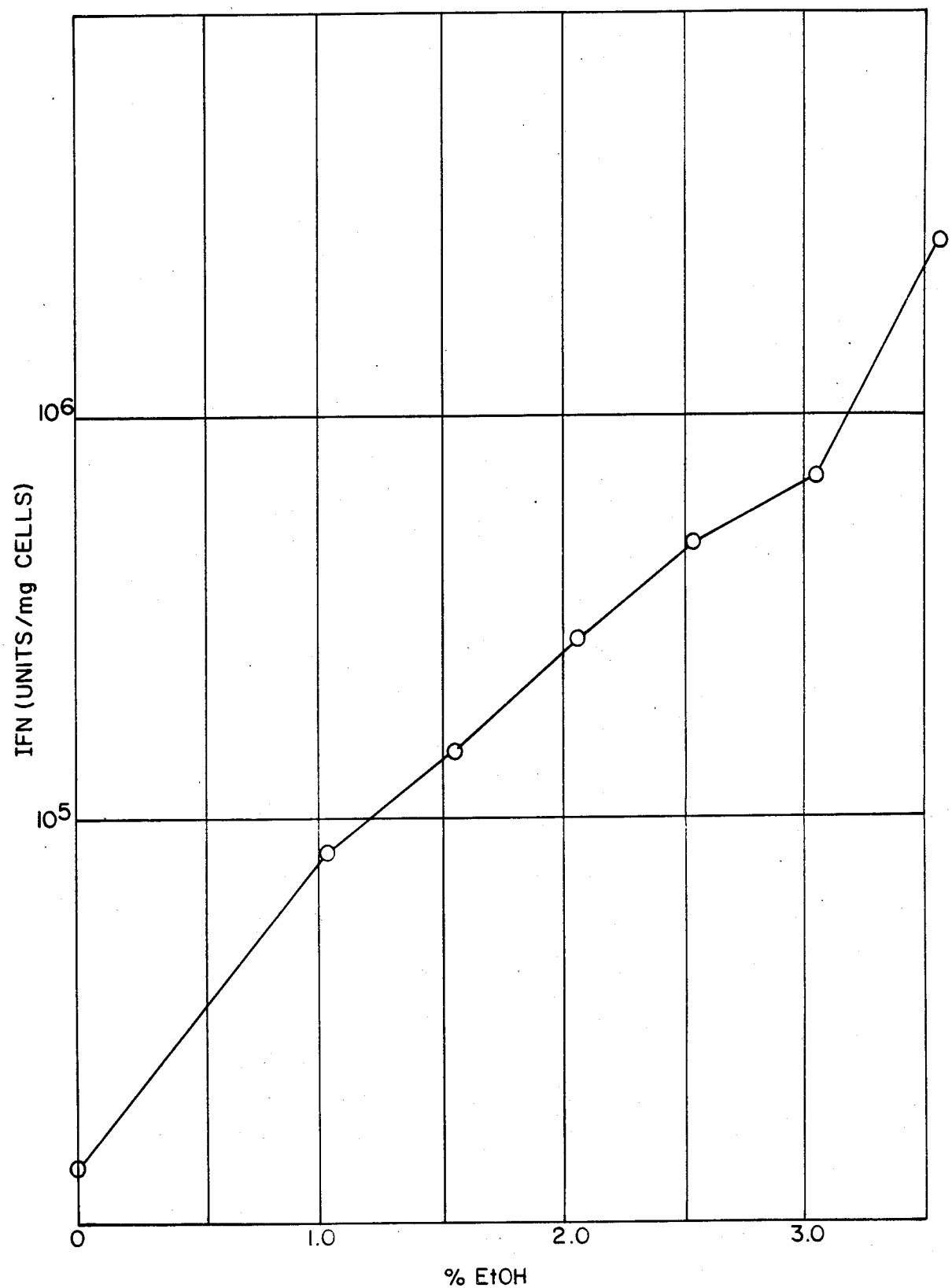
FIG. 1 is a graph of percent ethanol versus IFN-β activity showing the results of the experiments described in Example 1, infra.

As used herein, the term "heterologous" refers to polypeptides not produced by wild type bacteria. The heterologous polypeptides that are made by the invention process will typically have industrial, agricultural, or health care utility. In most instances, the polypeptides will be nonbacterial polypeptides that have amino acid sequences that are substantially identical to eukaryotic cell proteins or viral proteins. In this regard, the term "substantially identical" means that the amino acid sequences of the microbially produced synthetic polypeptide and the native polypeptide are either identical or differ by one or more amino acid alterations (deletions, additions, substitutions) that do not cause an adverse functional dissimilarity between the synthetic polypeptide and its native counterpart. Hydrophobic polypeptides of 15–30 Kd molecular weight having human therapeutic activity (e.g., IFN-α activity, IFN-β activity, IFN δ activity, colony stimulating factor (CSF) activity, tumor necrosis factor activity interleukin (IL-1, IL-2, or IL-3) activity and lymphotoxin activity) are of particular interest. For convenience, such polypeptides are referred to herein by their native designations (e.g., IFN-α, IFNβ, etc.) regardless of whether they are identical chemically to the native polypeptide.

The recombinant bacteria that are used in the invention may be made by recombinant DNA techniques. These techniques typically involve (i) cloning a synthetic structural gene or a structural gene of genomic origin that encodes the heterologous polypeptide into an appropriate plasmid or viral expression vector at a site which permits expression thereof (i.e., at a site controlled by a promoter-operator, a ribosome binding site for the translation of the transcribed mRNA, and a translation start codon in the same translational reading frame as the structural gene), (ii) introducing the vector into competent bacteria, and (iii) selecting recombinant cells (also called "transformants") either by a plasmid marker function or their ability to produce the heterologous polypeptide. E. coli or gram-negative bacteria that have metabolisms similar to E. coli are preferred. The heterologous polypeptide is generally present as an insoluble aggregate in the cytosol of E. coli transformants (i.e., it is a nonsecreted polypeptide).

The heterologous polypeptide-producing transformants are cultivated in a liquid nutrient medium. The medium comprises an excess of conventional nutrient materials that fulfill the cellular growth requirements of the bacteria, thereby enabling the bacteria to grow and multiply to a predetermined cellular density. Such materials will include sources of carbon and nitrogen for synthesis of cellular components and energy, and minerals (ions) such as sulfur ($SO_4^{-2}$), phosphorous ($PO_4^{-4}$), $Mg^{+2}$, $K^+$, $Cu^{++}$, $Zn^{++}$, $Mn^{++}$ and $Fe^{++}$. While one or more amino acids may be added to the medium initially, the protein hydrolysate that is used to enhance yield is not present initially. Oxygen will also be provided to the medium. In order to achieve maximum cellular densities, the cultivation will usually be carried out in a manner that enhances the area of the oxygen-liquid interface.

The yield enhancement achieved by the invention method is particularly pronounced when a low inoculum concentration is used in the cultivation. In this regard, the inoculum concentration will typically be in the range of 0.1 to 10 mg per liter, more usually about 0.1 to 1 mg per liter. Expressed in terms of inoculum volume per final volume of fermentation medium the inoculum condentration will usually be 0.1 to 10 v/v %, more usually 0.1 to 1 v/v %.

Important environmental factors affecting the cultivation include pH and temperature. The temperature will range betwen the minimum and maximum growth temperatures. Most bacteria exhibit maximum growth over a fairly narrow temperature range. For mesophilic bacteria, such as *E. coli*, the optimum temperature range is about 25° C. to about 42° C., preferably about 37° C. Most organisms will tolerate hydrogen ion concentration ranging over several pH units. For pathogenic bacteria, such as *E.coli*, the tolerable pH lies in the range of about 6 to 8, with 6.8 being preferred.

If the expression of the gene encoding the heterologous polypeptide is under the control of a repressible expression control sequence and it is desired to repress expression of that gene until a predetermined level of growth is achieved, the nutrient medium will also contain an appropriate repressor. For instance, if expression is under the control of the tryptophan (trp) promoter-operator, expression may be controlled by adding tryptophan to the medium. An excess of trypthophan may be added initially and then removed from the medium when the desired level of cellular growth has been achieved Alternatively, tryptophan is added in a predetermined amount that is correlated to the volume of nutrient medium and the approximate amount of tryptophan that would theoretically be in the cell mass in the volume at the desired level of growth. In the presence of excess preferred carbon source, such as glucose, the bacteria will use the tryptophan in the medium rather than producing it themselves for use in the production of cellular protein. While added tryptophan is present the bacteria repress expression of the heterologous polypeptide under the control of the trp promoter-operator. By initially adding a proper amount of tryptophan to the media the bacteria may be grown to a predetermined cellular density with the trp operator repressed. In order to determine this amount the volume of the medium must be known or determined, the amount of tryptophan per unit dry weight of the bacterial protein is determined experimentally or from published sources (for E.coli see Studies of Biosynthesis in Eschericia Coli, Roberts, et al, Carnegie Institution of Washington Publication 607 (1955), p28), and a desired cellular density is selected.

The alkanol and/or amino acid mixture are added to the nutrient medium during the terminal portion of the cultivation. The exact point in the cultivation at which these materials are added is not critical. In terms of the extent of bacterial growth, the alkanol and/or amino acid mixtue will usually be added when the cellular density (as measured in optical density (OD) units by a spectrophotometer at 680 nm) is at least about 2 OD units, preferably at least about 10 OD units. In instances where the expression of the gene encoding the polypeptide has been repressed, it is preferred to add the alkanol and/or amino acid mixture during the expression phase of the cultivation (i.e. the phase following derepression of the operator through removal or exhaustion of the repressor). The duration of the growth period after the alkanol/amino acid mixture is added may vary depending upon the particular bacteria, heterologous polypeptide, and cultivation conditions. Its duration will normally be in the range of about 1 to 5 hours. The cellular density at harvest will usually be in the range of 10 to 40 OD units, more usually 20 to 40 OD units.

The alkanols that may be used in the process are soluble in the aqueous nutrient medium and are not toxic to the bacteria at the concentrations at which they are added to the medium. These alkanols contain 1–4 carbon atoms and may be branched or straight chain. Preferred alkanols are straight chain (methanol, ethanol, n-propanol, and n-butanol). Ethanol is particularly preferred. The amount of alcohol added will typically be in the range of about 0.5% to 5% (v/v), preferably 1% to 3%. Mixtures of amino acids for use in supplementing the bacterial growth media are available commercially. These mixtures are typically protein hydrolysates that are made by subjecting naturally occurring proteinaceous materials, such as casein, soybean meal, lactalalbumin, animal tissue, and gelatin, to acid or enzymatic digestion. Alternatively, mixtures of amino acids may be made up from pure amino acid stocks. When the expression of the gene is under the control of the trp promoter-operator, the mixture of amino acids should lack tryptophan. Acid-hydrolyzed casein lacks tryptophan and is accordingly preferred for such systems. The amount of amino acid mixture added to the nutrient medium will usually be in the range of about 0.5% to 5% (w/v), preferably 1% to 3%. The alkanol and amino acids may be added to the nutrient medium separately or combined.

After harvest, the cells are processed to recover the heterologous polypeptide. This processing will normally involve disrupting the cells, separating crude heterologous polypeptide from bacterial proteins via one or more extraction steps, solubilizing the polypeptide (depending upon its hydrophobicity) and further purifying the polypeptide by gel filtration, high performance liquid chromatography or other protein purification procedures. Human lymphokines such as IFN-$\beta$ and IL-2 that are made by recombinant bacteria are preferably recovered from the cellular material in a reduced state and then oxidized to their native configuration.

Procedures for recovering and oxidizing IFN- and IL-2 are described in commonly owned U.S. application Ser. No. 353,360 filed Mar. 1, 1982, now U.S. Pat. No. 4,450,103, issued May 22, 1984; and commonly owned U.S. applications titled "Process for Recovering Microbially Produced Interleukin-2" U.S. Ser. No. 594,223, filed Mar. 28, 1984, now U.S. Pat. No. 4,569,790, issued Feb. 11, 1986 and "Controlled Oxidation of Microbially Produced Crysteine-Containing Proteins" U.S. Ser. No. 594,351, filed Mar. 28, 1984, now abandoned in lieu of U.S. Ser. No. 661,902, filed Oct. 17, 1984, now U.S. Pat. No. 4,530,787, issued July 23, 1985.

The following examples further describe the materials and techniques used in carrying out the invention. These examples are not intended to limited the invention in any manner.

EXAMPLE 1: EFFECT OF ETHANOL ON IFN-$\beta_{ser17}$ PRODUCTION

IFN-$\beta_{ser17}$ is a microbially produced mutein of IFN-$\beta$ in which the cysteine residue at amino acid position 17 is replaced with a serine residue. IFN-$\beta_{ser17}$ has two remaining cysteine residues: one at position 31 and the other at position 141. In native IFN-$\beta$ the cysteines at positions 31 and 141 interact to form a disulfide bridge. Commonly owned copending U.S. patent application Ser. No. 564,224, filed Dec. 20, 1983 describes the genetic engineering techniques that may be used to make genetically engineered E.coli that produce IFN-$\beta_{ser17}$.

IFN-$\beta_{ser17}$-producing E. coli were grown in the following medium:

| Ingredient | Approximate Initial Concentration |
|---|---|
| Na$_3$ Citrate.2H$_2$O | 3 mM |
| KH$_2$PO$_4$ | 30 mM |
| (NH$_4$)$_2$SO$_4$ | 74 mM |
| MgSO$_4$.7H$_2$O | 3 mM |
| MnSO$_4$.H$_2$O | 46 $\mu$M |
| ZnSO$_4$.7H$_2$O | 46 $\mu$M |
| CuSO$_4$.5H$_2$O | 1–2 $\mu$M |
| L-tryptophan | 50 mg/liter |
| FeSO$_4$.7H$_2$O | 74 $\mu$M |
| thiamine.HCl | 0.002% |
| glucose | 0.3% |

At late exponential phase inoculum from this culture (4%) was transferred to new flasks containing a similar medium minus tryptophan and with varying amounts of ethanol. At the end of growth (as estimated by turbidity readings), samples were taken for IFN-β activity using a standard cytopathic effect (CPE) assay. FIG. 1 shows the results of these tests. As shown, addition of 3% ethanol increases IFN-β activity about one and one-half log units.

EXAMPLE 2: EFFECT OF ETHANOL ON IL-2 AND IL-2$_{ser125}$ PRODUCTION

IL-2$_{ser125}$ is a microbially produced mutein of human IL-2 in which the cysteine residue at amino acid position 125 is replaced with a serine residue. Commonly owned copending U.S. patent application Ser. No. 564,224, now U.S. Pat. No. 4,518,584, issued May 21, 1985 describes the procedures that may be used to make E. coil that produce IL-2 or IL-2$_{ser125}$.

Frozen tubes of IL-2 and IL-2$_{ser125}$-producing E.coli strains grown to 1-2 OD$_{680}$ in Brain Heart infusion seed medium +50 mg/l L-tryptophan, 5 mg/l tetracycline, were thawed and used to inoculate flasks of seed medium at 1% (v/v) level. The composition of the seed medium was:

| Seed Medium | |
|---|---|
| NH$_4$Cl | 10 mM |
| KH$_2$PO$_4$ | 21.9 mM |
| Na$_2$HPO$_4$ | 28.1 mM |
| K$_2$SO$_4$ | 9 mM |
| MgSO$_4$ | 0.2 mM |
| TK-9* | 0.1 ml/liter |
| Sterile Additions | |
| 50% Glucose | 4 ml/liter = 2 g/liter |
| 1% Thiamine HCl | 1 ml/liter = 10 mg/liter |
| 0.5% L-tryptophan | 1 ml/100 ml = 50 mg/liter |
| 4 mM FeSO$_4$ | 0.25 ml/100 ml = 10 μM |
| 1% tetracycline | 50 μl/100 ml = 5 mg/liter |

*TK-9:
30 mM ZnSO$_4$
30 mM MnSO$_4$
1 mM CuSO$_4$

The seed cultures were shaken at 37° C. until an OD$_{680}$ of 0.5–1.5 was reached (about 6 hr). These seed cultures were used to inoculate the following cultivation medium in a 10 liter fermenter.

| Cultivation Medium | | |
|---|---|---|
| (NH$_4$)$_2$SO$_4$ | 150 mM | |
| KH$_2$PO$_4$ | 21.6 mM | |
| Na$_3$ Citrate | 1.5 mM | |
| TK-9 | 2 ml/liter | |
| pH adjust to 6.5 with NaOH | | |
| Vol → 8.5 liter | | |
| Sterilize | | |
| Sterile Additions: | | |
| | Vol. Added | Conc. |
| 50% Glucose | 100 ml | 5 g/liter |
| 1% Thiamine HCl | 20 ml | 20 mg/liter |
| 0.5% L-tryptophan | 140 ml | 70 mg/liter |
| 0.2 M FeSO$_4$ | 5 ml | 100 μM |
| 0.5 M MgSO$_4$ | 60 ml | 3 mM |
| 1% tetracycline* | 5 ml | 5 mg/liter |

(These are each added separately from the other sterile additions.)
pH Control: 5 N KOH (50% glucose feed linked)
*Tetracycline made fresh in 100% ethanol.

Just prior to inoculation the pH was brought to 6.8 and maintained there throughout the run, using 5 N KOH. A 50% glucose solution was fed in conjuction with alkali demand to maintain the residual glucose at approximately 5–10 g/liter. The oxygen demand of the culture was met as follows: from the initial conditions of 350 rpm and no air sparging, the rpm was first ranged up to 1200, followed by increasing the airflow to 5 liter/min, followed by sparging oxygen, to keep the dissolved oxygen at about 40% of air saturation.

The amount of tryptophan added was sufficient to repress IL-2 production until 8–10 O.D.$_{680}$. Growth rate of the culture was about 0.6 to 0.7 hr$^{-1}$. After that, high expression began, and the cells continued to grow at a reduced rate (0.4–0.5 hr$^{-1}$). When an O.D.$_{680}$ of 40–50 was reached, 20 g/liter (267 ml/fermenter) ethanol was added. The cells were harvested 3 hr after ethanol addition (usually 19–20 hr after incubation).

As compared to control fermentations carried out without adding ethanol to the cultivation medium, addition of ethanol resulted in about a 2-fold increase in production of IL-2 or IL-2$_{ser125}$, as the case may be. Analysis of harvest samples from the fermentations showed that the average yield per 10 liter fermenter was 8.3 g IL-2 and 5.6 g IL-2$_{ser125}$.

EXAMPLE 3: EFFECT OF ETHANOL AND CASAMINO ACIDES (CAA) ON IL-2$_{ser125}$ PRODUCTION Frozen tubes of IL-2$_{ser125}$-producing E. coli (Example 2) were thawed and inoculated directly into four fermentation tanks (A, B, C, D) containing the following fermentation medium to a level of 2 mg cell dry wt/liter.

| | |
|---|---|
| (NH$_4$)$_4$SO$_4$ | 150 mM |
| KH$_2$PO$_4$ | 21.6 mM |
| Na$_3$ Citrate | 15.0 mM |
| TK9 | 2 ml/liter |
| pH adjusted to 6.5 with 2.5 N NaOH | |
| autoclaved | |
| Sterile Additions (post autoclave) | |
| MgSO$_4$.7H$_2$O | 3 mM |
| FeSO$_4$ | 100 μM |
| L-tryptophan | 14 mg/liter |
| Thiamine HCl | 20 mg/liter |
| Glucose | 5 g/liter |
| Tetracycline | 5 mg/liter |

The operating pH of the fermenters was maintained with 5 N KOH at 6.8. A 50% glucose feed was triggered by base addition requirements. Residual glucose in the fermenters was maintained between 5–10 g/liter. Dissolved oxygen in the fermenters was maintained at 40% through agitation to a maximum of 1200 rpm, then through air sparging to a maximum of 2 liters per min. Oxygen sparging was then used to 4 liters per min.

CAA (a 20% stock solution of autoclaved amino acids) were added to the fermenter when the turbidity equaled about 10 O.D. Growth rate between 1 and 10 O.D. is typically about u=0.60–0.70 hr$^{-1}$. Full induction with 14 mg/liter tryptophan occurs around 1–2 O.D. By the time the CAA were added to the fermenters, expression of IL-2$_{ser125}$ was fully turned on.

One percent CAA was added to tank "A". To the rest of the tanks 2% CAA was added. No ethanol was added to either tank "A" or "B". Two percent ethanol was added to tank "C", and 3% ethanol was added to tank "D", approximately 2 hr after CAA addition (20 O.D.).

Optical density, activity, and IL-2 protein measurements were made at various stages of the fermentations. Culture protein was estimated from optical density, and IL-2 protein from gel scans of crude extracts. Specific activity for IL-2 was calculated by combining the activity data with the gel scans. For comparison, a harvest sample taken from a fermentation lacking CAA addition was run concurrently on the gel.

These measurements are reported in Table 1 below.

TABLE 1

|  | O.D. | Total U/mg Protein | U/Ferm. | % Total Protein | g IL-2/Ferm. | Specific Activity U/mg IL-2 |
|---|---|---|---|---|---|---|
| Tank A | | | | | | |
| 11.6 hrs | 6.6 | $4.498 \cdot 10^4$ | $9.353 \cdot 10^8$ | — | — | |
| 12.3 | 10.0 | $5.155 \cdot 10^4$ | $1.624 \cdot 10^9$ | 2.1 | 0.66 | $2.4 \times 10^6$ |
| 13.3 | 16.5 | $1.111 \cdot 10^5$ | $5.773 \cdot 10^9$ | 2.9 | 1.5 | $3.8 \times 10^6$ |
| 14.3 | 27.5 | $1.652 \cdot 10^5$ | $1.431 \cdot 10^{10}$ | 5.4 | 4.7 | $3.0 \times 10^6$ |
| 15.3 | 28.6 | $1.546 \cdot 10^5$ | $1.393 \cdot 10^{10}$ | 5.0 | 4.5 | $3.1 \times 10^6$ |
| 16.3 | 30.6 | $7.147 \cdot 10^4$ | $6.889 \cdot 10^9$ | 6.1 | 5.9 | $1.17 \times 10^6$ |
| Tank B | | | | | | |
| 11.6 | 7.55 | $2.824 \cdot 10^4$ | $6.717 \cdot 10^8$ | — | — | |
| 12.3 | 11.65 | $5.764 \cdot 10^4$ | $2.115 \cdot 10^9$ | 2.9 | 0.91 | $2.3 \times 10^6$ |
| 13.3 | 17.4 | $1.224 \cdot 10^4$ | $6.820 \cdot 10^9$ | — | — | |
| 14.3 | 26.2 | $2.306 \cdot 10^4$ | $1.903 \cdot 10^{10}$ | 7.0 | 5.8 | $3.3 \times 10^6$ |
| 15.3 | 32.8 | $4.054 \cdot 10^4$ | $4.188 \cdot 10^9$ | 5.9 | 6.1 | $6.87 \times 10^5$ |
| 16.3 | 36.2 | $1.2161 \cdot 10^5$ | $1.387 \cdot 10^{10}$ | 7.6 | 8.7 | $1.59 \times 10^6$ |
| Tank C | | | | | | |
| 11.6 | 6.3 | $5.343 \cdot 10^4$ | $1.060 \cdot 10^9$ | — | — | |
| 12.3 | 9.65 | $6.374 \cdot 10^4$ | $1.937 \cdot 10^9$ | 2.4 | 0.73 | $2.65 \times 10^6$ |
| 13.3 | 14.6 | $9.443 \cdot 10^4$ | $4.343 \cdot 10^9$ | — | — | |
| 14.3 | 19.7 | $2.067 \cdot 10^5$ | $1.283 \cdot 10^{10}$ | 7.1 | 4.4 | $2.92 \times 10^6$ |
| 15.3 | 22.5 | $6.186 \cdot 10^4$ | $4.384 \cdot 10^9$ | 9.4 | 6.6 | $6.64 \times 10^5$ |
| 16.3 | 24.2 | $2.474 \cdot 10^5$ | $1.886 \cdot 10^{10}$ | 9.0 | 6.9 | $2.73 \times 10^6$ |
| 17.3 | 28.0 | — | — | 8.6 | 7.6 | |
| Tank D | | | | | | |
| 11.6 | 5.95 | $4.374 \cdot 10^4$ | $8.20 \cdot 10^8$ | — | — | |
| 12.3 | 9.35 | $3.468 \cdot 10^4$ | $1.021 \cdot 10^9$ | 2.1 | 0.62 | $1.65 \times 10^6$ |
| 13.3 | 12.7 | $1.111 \cdot 10^5$ | $4.443 \cdot 10^9$ | — | — | |
| 14.3 | 16.5 | $2.221 \cdot 10^5$ | $1.155 \cdot 10^{10}$ | 5.4 | 2.8 | $4.13 \times 10^6$ |
| 15.3 | 22.0 | $2.067 \cdot 10^5$ | $1.432 \cdot 10^{10}$ | 10.6 | 7.3 | $1.96 \times 10^6$ |
| 16.3 | 23.0 | $1.730 \cdot 10^5$ | $1.253 \cdot 10^{10}$ | 8.1 | 5.9 | $2.12 \times 10^6$ |
| 17.3 | 24.9 | — | — | 10.6 | 8.3 | |
| 18.3 | 26.4 | — | — | 10.7 | 8.9 | |
| Comparison | 45 | — | — | 3.6 | 5.1 | |

As shown by the data in the table, the addition of CAA increased the yield of total protein from 3.6% to 7.6% (2% CAA) and 6.1% (1% CAA). Qualitatively, 2% CAA gives significantly more IL-2 than 1%. Also, addition of ethanol (tanks C and D) improves the production of IL-2 over fermentations without ethanol (A and B).

FIG. 2 shows the growth kinetics of the four fermentations.

EXAMPLE 4: EFFECT OF ETHANOL ON IFN-α PRODUCTION

IFN-α6L is a human alpha interferon that is produced by recombinant *E. coli*. It is the subject of commonly owned, copending application Ser. No. 409,123 filed Aug. 18, 1982. The disclosure of that application is incorporated herein by reference to the extent necessary to satisfy 35 USC 112.

Recombinant *E. coli* that produce an IFN-α6L were grown in a cultivation medium supplemented with ethanol at a level of 30 g/liter cultivation medium using procedures similar to the cultivation in the absence of ethanol, the ethanol addition resulted in a ½ to 1 log increase in yield of IFN-α6L.

Samples of the IFN-$\beta_{ser17}$-producing and IL-$2_{ser125}$-producing *E. coli* strains were deposited in the American Type Culture Collection (ATCC), 12301 Parklawn Drive, Rockville, Md. 20852 USA. The deposit dates and accession numbers for these samples are listed below.

| Protein Produced | Deposit Date | Accession Number |
|---|---|---|
| IFN-$\beta_{ser17}$ | 18 November 1983 | 39517 |
| IL-$2_{ser125}$ | 18 November 1983 | 39516 |
| IL-$2_{Ser125}$* | 26 September 1983 | 39542 |
| IL-$2_{ser125}$* | 6 March 1984 | 39626 |

*This protein also lacks the initial alanine of the native protein.

The expression of the genes encoding IFN-$\beta_{ser17}$, IL-2, and IL-$2_{ser125}$ in the recombinant bacteria described in Examples 1–3 is under the control of the trp promoter-operator.

Modifications of the above-described modes for carrying out the invention that are obvious to those of skill in biochemical engineering and related fields are intended to be within the scope of the following claims.

We claim:

1. In a method of improving the yield of heterologous proteins selected from the group consisting of proteins having IFN-alpha activity, IFN-beta activity, IFN-gamma activity, colony stimulating factor (CSF) activity, tumor necrosis factor activity, interleukin (IL-1, IL-2, or IL-3) activity and lymphotoxin activity, produced by cultivating recombinant *E. coli* in a liquid nutrient medium, the improvement comprising:

supplementing the medium with a composition that supports bacterial growth during the terminal portion of the cultivation, said composition being selected from the group consisting of from about 0.5% to 5% (v/v) of ethanol; from about 0.5 to 5% (w/v) of a mixture of amino acids, and mixtures thereof, wherein said composition is added to the medium when the cellular density of the culture (as measured in optical density (OD) units by a spectrophotometer at 680 nm) is at least about 2 OD units.

2. The method of claim 1 wherein the protein is a hydrophobic nonsecreted protein that has human lymphokine activity.

3. The method of claim 1 wherein the mixture of amino acids is a protein hydrosylate.

4. The method of claim 1 wherein the inoculum concentration is 0.1 to 10 v/v %.

5. The method of claim 2 wherein the inoculum concentration is 0.1 to 1 v/v %.

6. The method of claim 1 wherein the composition is added to the media when the cellular density of the culture (as measured in optical density (OD units) by a spectrophotometer at 680 nm) is at least 10.

7. The method of improving the yield of the heterologous protein IFN-$\beta$, produced by cultivating recombinant *E. coli* transformed with an expression vector which encodes for the IFN-$\beta$ protein and under the control of the trp operator-promoter in a liquid nutrient medium wherein the inoculum concentration is 0.1 to 1 v/v % and a composition that supports bacterial growth during the terminal portion of the cultivation, and composition comprising from about 0.5% to 5 (w/v) of an acid hydrolyzed casein, wherein said composition is added to the medium when the cellular density of the culture (as measured in optical density (OC) units by a spectrophotometer at 680 nm is at least 10 OD units.

8. The method of claim 7, wherein the IFN-$\beta$ is an IFN-$\beta_{ser17}$.

9. A method of improving the yield of the heterologous protein IL-2, produced by cultivating recombinant *E. coli* transformed with an expression vector which encodes for the IL-2 protein and under the control of the trp operator-promoter in a liquid nutrient medium wherein the inoculum concentration is 0.1 to 1 v/v % and a composition that supports bacterial growth during the terminal portion of the cultivation, said composition comprising from about 0.5 to 5 (w/v) of an acid hydrolyzed casing wherein said composition is added to the medium when the cellular density of the culture as measured in optical density (OD) units by a spectrophotometer at 680 nm is at least 10 OD units.

10. The method of claim 9 wherein the IL-2 is an IL-$2_{ser125}$.

* * * * *